United States Patent
Ben-David et al.

(10) Patent No.: US 8,718,791 B2
(45) Date of Patent: May 6, 2014

(54) ELECTRODE CUFFS

(75) Inventors: Tamir Ben-David, Tel Aviv (IL); Shai Ayal, Shoham (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 600 days.

(21) Appl. No.: 12/947,608

(22) Filed: Nov. 16, 2010

(65) Prior Publication Data

US 2011/0098796 A1    Apr. 28, 2011

Related U.S. Application Data

(63) Continuation-in-part of application No. 12/217,930, filed on Jul. 9, 2008, now abandoned, and a continuation-in-part of application No. 11/070,842, filed on Feb. 24, 2005, now Pat. No. 8,386,056, which is a continuation of application No. 10/719,659, filed on Nov. 20, 2003, now Pat. No. 7,778,711, which is a continuation-in-part of application No. PCT/IL03/00431, filed on May 23, 2003.

(51) Int. Cl.
*A61N 1/05* (2006.01)

(52) U.S. Cl.
USPC .......................................................... 607/118

(58) Field of Classification Search
USPC .......................................................... 607/118
See application file for complete search history.

(56) References Cited

U.S. PATENT DOCUMENTS

| | | |
|---|---|---|
| 4,010,755 A | 3/1977 | Preston |
| 4,026,300 A | 5/1977 | DeLuca et al. |
| 4,161,952 A | 7/1979 | Kinney et al. |
| 4,535,785 A | 8/1985 | van den Honert et al. |
| 4,573,481 A | 3/1986 | Bullara |
| 4,602,624 A | 7/1986 | Naples et al. |
| 4,608,985 A | 9/1986 | Crish et al. |
| 4,628,942 A | 12/1986 | Sweeney et al. |
| 4,649,936 A | 3/1987 | Ungar et al. |
| 5,095,905 A | 3/1992 | Klepinski |

(Continued)

FOREIGN PATENT DOCUMENTS

| | | |
|---|---|---|
| DE | 198 47 446 | 4/2000 |
| EP | 0 688 577 | 12/1995 |

(Continued)

OTHER PUBLICATIONS

An Office Action dated Jun. 8, 2012, which issued during the prosecution of U.S. Appl. No. 12/228,630.

(Continued)

*Primary Examiner* — Tammie K Heller
(74) *Attorney, Agent, or Firm* — Sughrue Mion, PLLC

(57) ABSTRACT

Apparatus is provided for application to a nerve of a subject, including an electrode cuff, which includes a housing, which is configured to be placed at least partially around the nerve so as to define an inner surface of the housing that faces the nerve. A plurality of insulating elements are coupled to the inner surface of the housing at respective insulating element longitudinal positions along the housing, such that the inner surface of the housing and pairs of the insulating elements define one or more respective cavities at respective cavity longitudinal positions along the housing. One or more electrodes are fixed to the housing in fewer than all of the cavities, such that at least one of the cavities is an empty cavity that does not have an electrode positioned therein. Other embodiments are also described.

17 Claims, 8 Drawing Sheets

(56) References Cited

U.S. PATENT DOCUMENTS

| | | |
|---|---|---|
| 5,143,067 A | 9/1992 | Rise et al. |
| 5,170,802 A | 12/1992 | Mehra |
| 5,199,430 A | 4/1993 | Fang et al. |
| 5,203,326 A | 4/1993 | Collins |
| 5,215,086 A | 6/1993 | Terry, Jr. et al. |
| 5,224,491 A | 7/1993 | Mehra |
| 5,243,980 A | 9/1993 | Mehra |
| 5,282,468 A | 2/1994 | Klepinski |
| 5,334,221 A | 8/1994 | Bardy |
| 5,344,438 A | 9/1994 | Testerman et al. |
| 5,356,425 A | 10/1994 | Bardy et al. |
| 5,400,784 A | 3/1995 | Durand et al. |
| 5,411,531 A | 5/1995 | Hill et al. |
| 5,423,872 A | 6/1995 | Cigaina |
| 5,487,756 A | 1/1996 | Kallesoe et al. |
| 5,505,201 A | 4/1996 | Grill et al. |
| 5,507,784 A | 4/1996 | Hill et al. |
| 5,628,777 A | 5/1997 | Moberg et al. |
| 5,634,462 A | 6/1997 | Tyler et al. |
| 5,690,681 A | 11/1997 | Geddes et al. |
| 5,700,282 A | 12/1997 | Zabara |
| 5,755,750 A | 5/1998 | Petruska et al. |
| 5,800,470 A | 9/1998 | Stein et al. |
| 5,824,027 A | 10/1998 | Hoffer et al. |
| 5,833,664 A | 11/1998 | Seare, Jr. |
| 5,893,881 A | 4/1999 | Elsberry et al. |
| 5,916,239 A | 6/1999 | Geddes et al. |
| 5,919,220 A | 7/1999 | Stieglitz et al. |
| 5,938,596 A | 8/1999 | Woloszko et al. |
| 6,006,134 A | 12/1999 | Hill et al. |
| 6,038,477 A | 3/2000 | Kayyali |
| 6,073,048 A | 6/2000 | Kieval et al. |
| H1905 H | 10/2000 | Hill |
| 6,161,029 A | 12/2000 | Spreigl et al. |
| 6,178,349 B1 | 1/2001 | Kieval |
| 6,230,061 B1 | 5/2001 | Hartung |
| 6,292,695 B1 | 9/2001 | Webster, Jr. et al. |
| 6,292,703 B1 | 9/2001 | Meier et al. |
| 6,298,268 B1 | 10/2001 | Ben-Haim et al. |
| 6,308,105 B1 | 10/2001 | Duysens et al. |
| 6,317,631 B1 | 11/2001 | Ben-Haim et al. |
| 6,341,236 B1 | 1/2002 | Osorio et al. |
| 6,363,279 B1 | 3/2002 | Ben-Haim et al. |
| 6,445,953 B1 | 9/2002 | Bulkes et al. |
| 6,456,866 B1 | 9/2002 | Tyler et al. |
| 6,463,324 B1 | 10/2002 | Ben-Haim et al. |
| 6,542,774 B2 | 4/2003 | Hill et al. |
| 6,564,096 B2 | 5/2003 | Mest |
| 6,600,956 B2 | 7/2003 | Maschino et al. |
| 6,611,713 B2 | 8/2003 | Schauerte |
| 6,628,987 B1 | 9/2003 | Hill et al. |
| 6,684,105 B2 | 1/2004 | Cohen et al. |
| 6,712,772 B2 | 3/2004 | Cohen et al. |
| RE38,705 E | 2/2005 | Hill et al. |
| 6,850,801 B2 | 2/2005 | Kieval et al. |
| 6,865,416 B2 | 3/2005 | Dev et al. |
| 6,866,657 B2 | 3/2005 | Shchervinsky |
| 6,907,295 B2 | 6/2005 | Gross et al. |
| 6,934,583 B2 | 8/2005 | Weinberg et al. |
| 6,937,897 B2 | 8/2005 | Min et al. |
| 6,985,774 B2 | 1/2006 | Kieval et al. |
| 7,020,530 B1 | 3/2006 | Ideker et al. |
| 7,027,876 B2 | 4/2006 | Casavant et al. |
| 7,087,053 B2 | 8/2006 | Vanney |
| 7,113,816 B2 | 9/2006 | Matsukawa et al. |
| 7,123,961 B1 | 10/2006 | Kroll et al. |
| 7,139,607 B1 | 11/2006 | Shelchuk |
| 7,167,748 B2 | 1/2007 | Ben-Haim et al. |
| 7,212,870 B1 | 5/2007 | Helland |
| 7,218,971 B2 | 5/2007 | Heil et al. |
| 7,225,016 B1 | 5/2007 | Koh |
| 7,236,821 B2 | 6/2007 | Cates et al. |
| 7,245,967 B1 | 7/2007 | Shelchuk |
| 7,248,930 B1 | 7/2007 | Woloszko et al. |
| 7,269,457 B2 | 9/2007 | Shafer et al. |
| 7,321,793 B2 | 1/2008 | Ben-Ezra et al. |
| 7,346,398 B2 | 3/2008 | Gross et al. |
| 7,460,906 B2 | 12/2008 | Libbus |
| 7,584,004 B2 | 9/2009 | Caparso et al. |
| 7,778,703 B2 | 8/2010 | Gross et al. |
| 7,809,442 B2 | 10/2010 | Bolea et al. |
| 7,840,266 B2 | 11/2010 | Libbus et al. |
| 7,996,092 B2 | 8/2011 | Mrva et al. |
| 8,155,757 B1 | 4/2012 | Neisz et al. |
| 8,214,056 B2 | 7/2012 | Hoffer et al. |
| 2002/0099419 A1 | 7/2002 | Cohen et al. |
| 2002/0161415 A1 | 10/2002 | Cohen et al. |
| 2003/0045909 A1 | 3/2003 | Gross et al. |
| 2003/0045914 A1 | 3/2003 | Cohen et al. |
| 2003/0050677 A1 | 3/2003 | Gross et al. |
| 2003/0097221 A1 | 5/2003 | Chun et al. |
| 2003/0100933 A1 | 5/2003 | Ayal et al. |
| 2004/0006311 A1 | 1/2004 | Shchervinsky |
| 2004/0006331 A1 | 1/2004 | Shchervinsky |
| 2004/0193231 A1 | 9/2004 | David et al. |
| 2004/0199210 A1 | 10/2004 | Shelchuk |
| 2004/0254612 A1 | 12/2004 | Ezra et al. |
| 2005/0010265 A1 | 1/2005 | Baru Fassio et al. |
| 2005/0065553 A1 | 3/2005 | Ben-Ezra et al. |
| 2005/0131467 A1 | 6/2005 | Boveja |
| 2005/0149154 A1 | 7/2005 | Cohen et al. |
| 2005/0187584 A1 | 8/2005 | Denker et al. |
| 2005/0197675 A1 | 9/2005 | David et al. |
| 2005/0261672 A1 | 11/2005 | Deem et al. |
| 2005/0267542 A1 | 12/2005 | David et al. |
| 2005/0273138 A1 | 12/2005 | To et al. |
| 2006/0052831 A1 | 3/2006 | Fukui |
| 2006/0074449 A1 | 4/2006 | Denker et al. |
| 2006/0100668 A1 | 5/2006 | Ben-David et al. |
| 2006/0106441 A1 | 5/2006 | Ayal et al. |
| 2006/0136024 A1 | 6/2006 | Cohen et al. |
| 2006/0167501 A1 | 7/2006 | Ben-David et al. |
| 2006/0195170 A1 | 8/2006 | Cohen et al. |
| 2006/0206153 A1 | 9/2006 | Libbus et al. |
| 2006/0206154 A1 | 9/2006 | Moffitt et al. |
| 2006/0206155 A1 | 9/2006 | Ben-David et al. |
| 2006/0206159 A1 | 9/2006 | Moffitt et al. |
| 2006/0217772 A1 | 9/2006 | Libbus et al. |
| 2006/0229677 A1 | 10/2006 | Moffitt et al. |
| 2006/0241697 A1 | 10/2006 | Libbus et al. |
| 2006/0241725 A1 | 10/2006 | Libbus et al. |
| 2006/0241733 A1 | 10/2006 | Zhang et al. |
| 2006/0247607 A1 | 11/2006 | Cornelius et al. |
| 2006/0265027 A1 | 11/2006 | Vaingast et al. |
| 2006/0271108 A1 | 11/2006 | Libbus et al. |
| 2006/0271115 A1 | 11/2006 | Ben-Ezra et al. |
| 2006/0271137 A1 | 11/2006 | Stanton-Hicks |
| 2006/0282145 A1 | 12/2006 | Caparso et al. |
| 2007/0150034 A1 | 6/2007 | Rooney et al. |
| 2007/0162079 A1 | 7/2007 | Shemer et al. |
| 2007/0179543 A1 | 8/2007 | Ben-David et al. |
| 2007/0179558 A1 | 8/2007 | Gliner et al. |
| 2007/0203527 A1 | 8/2007 | Ben-David et al. |
| 2007/0239243 A1 | 10/2007 | Moffitt et al. |
| 2007/0255320 A1 | 11/2007 | Inman et al. |
| 2008/0004673 A1 | 1/2008 | Rossing et al. |
| 2008/0021504 A1 | 1/2008 | McCabe et al. |
| 2008/0065158 A1 | 3/2008 | Ben-Ezra et al. |
| 2008/0065184 A1 | 3/2008 | Hoffer et al. |
| 2008/0086180 A1 | 4/2008 | Ben-Ezra et al. |
| 2008/0086185 A1 | 4/2008 | Amurthur et al. |
| 2008/0109045 A1 | 5/2008 | Gross et al. |
| 2008/0132983 A1 | 6/2008 | Cohen et al. |
| 2008/0172116 A1 | 7/2008 | Mrva et al. |
| 2008/0234780 A1 | 9/2008 | Smith et al. |
| 2009/0005845 A1 | 1/2009 | David et al. |
| 2009/0259315 A1 | 10/2009 | Banik |
| 2009/0275996 A1 | 11/2009 | Burnes et al. |
| 2010/0010603 A1 | 1/2010 | Ben-David et al. |
| 2010/0047376 A1 | 2/2010 | Imbeau et al. |
| 2010/0241195 A1 | 9/2010 | Meadows et al. |
| 2010/0241207 A1 | 9/2010 | Bluger |
| 2010/0312320 A1 | 12/2010 | Faltys et al. |
| 2011/0160827 A1 | 6/2011 | Bonde et al. |

(56) References Cited

U.S. PATENT DOCUMENTS

| | | | |
|---|---|---|---|
| 2011/0196445 | A1 | 8/2011 | Bolea et al. |
| 2011/0202106 | A1 | 8/2011 | Bolea et al. |
| 2012/0095540 | A1 | 4/2012 | Wahlstrand et al. |
| 2012/0130463 | A1 | 5/2012 | Ben-David |
| 2012/0197371 | A1 | 8/2012 | Neisz et al. |

FOREIGN PATENT DOCUMENTS

| | | |
|---|---|---|
| EP | 0 865 800 | 9/1998 |
| EP | 1 785 160 | 5/2007 |
| WO | WO 01/10357 | 2/2001 |
| WO | WO 01/10375 | 2/2001 |
| WO | WO 02/22206 | 3/2002 |
| WO | WO 02/087683 | 11/2002 |
| WO | WO 03/018113 | 3/2003 |
| WO | WO 03/094693 | 11/2003 |
| WO | WO 03/099373 | 12/2003 |
| WO | WO 03/099377 | 12/2003 |
| WO | WO 2004/028624 | 4/2004 |
| WO | WO 2004/047914 | 6/2004 |
| WO | WO 2004/052444 | 6/2004 |
| WO | WO 2004/103455 | 12/2004 |
| WO | WO 2004/110549 | 12/2004 |
| WO | WO 2004/110550 | 12/2004 |
| WO | WO 2006/126201 | 11/2006 |
| WO | WO 2007/053065 | 5/2007 |
| WO | WO 2008/007360 | 1/2008 |

OTHER PUBLICATIONS

An Office Action dated Aug. 21, 2012, which issued during the prosecution of U.S. Appl. No. 13/271,720.

An Office Action dated Jul. 30, 2012, which issued during the prosecution of U.S. Appl. No. 11/978,440.

Office Action dated Dec. 2, 2011 issued in U.S. Appl. No. 12/012,366.

Office Action dated Sep. 28, 2011 issued in U.S. Appl. No. 12/228,630.

Vincenzi, et al., "Release of autonomic mediators in cardiac tissue by direct subthreshold electrical stimulation", J Pharmacol Exp Ther. Aug. 1963; 141:185-94.

Quan KJ, et al., "Endocardial stimulation of efferent parasympathetic nerves to the atrioventricular node in humans: optimal stimulation sites and the effects of digoxin", Journal of Interventional Cardiac Ekectrophysiology 5:145-152, 2001.

Lemery R et al., "Feasibility study of endocardial mapping of ganglionated plexuses during catheter ablation of atrial fibrillation", Heart Rhythm 3:387-396, 2006.

Wallick DW et al., "Selective AV nodal vagal stimulation improves hemodynamics during acute atrial fibrillation in dogs", AM J Physiol Heart Circ Physiol 281:H1490-H1497, 2001.

Zhang Y et al., "Chronic atrioventricular nodal vagal stimulation: first evidence for long-term ventricular rate control in canine atrial fibrillation model", Circulation 112:2904-2911, 2005.

Schauerte P et al., "Ventricular rate control during atrial fibrillation by cardiac parasympathetic nerve stimulation: A transvenous approach", Journal of the American College of Cardiology 34(7): 2043-2050, 1999.

Schauerte P et al., "Catheter stimulation of cardiac parasympathetic nerves in humans: A novel approach to the cardiac autonomic nervous system", Circulation 104: 2430-2435, 2001.

Schauerte P et al., "Transvenous parasympathetic cardiac nerve stimulation for treatment of tachycardiac atrial fibrillation", Tachycarde Rhythmusstorungen 89:766-773, 2000.

Lazzara R et al., "Selective in situ parasympathetic control of the canine sinuatrial and atrioventricular node", Circulation Research 32:393-401, 1973.

Chen SA, et al., "Intracardiac stimulation of human parasympathetic nerve fibers induces negative dromotropic effects: implication with the lesions of radiofrequency catheter ablation", Journal of Cardiovascular Electrophysiology 9(3):245-52, 1998.

Bluemel KM, "Parasympathetic postganglionic pathways to the sinoatrial node," J Physiol. 259(5 Pt 2):H1504-10 (1990).

Cooper et al., "Neural effects on sinus rate and atrial ventricular conduction produced by electrical stimulation from a transvenous electrode catheter in the canine right pulmonary artery" Circ Res vol. 46(1):48-57 (1980).

Goldberger JJ et al., "New technique for vagal nerve stimulation," J Neurosci Methods. 91(1-2):109-14 (1999).

Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.

Tarver W B et al., "Clinical experience with a helical bipolar stimulating lead", Pace, vol. 15, Oct., Part 11 (1992).

Naples GG et al., "A spiral nerve cuff electrode for peripheral nerve stimulation," by IEEE Transactions on Biomedical Engineering, 35(11) (1988).

Fitzpatrick et al., in "A nerve cuff design for the selective activation and blocking of myelinated nerve fibers," Ann. Conf. of the IEEE Eng. in Medicine and Biology Soc, 13(2), 906 (1991).

Baratta R et al., "Orderly stimulation of skeletal muscle motor units with tripolar nerve cuff electrode," IEEE Transactions on Biomedical Engineering, 36(8):836-43 (1989).

Deurloo KE et al., "Transverse tripolar stimulation of peripheral nerve: a modelling study of spatial selectivity," Med Biol Eng Comput, 36(1):66-74 (1998).

Takei M et al., "Vagal stimulation prior to atrial rapid pacing protects the atrium from electrical remodeling in anesthetized dogs," Jpn Circ J 65(12):1007-81 (2001).

Hayashi H et al., "Different effects of class Ic and III antiarrhythmic drugs on vagotonic atrial fibrillation in the canine heart," Journal of Cardiovascular Pharmacology 31:101-107 (1998).

Masato Tsuboi et al., "Inotropic, chronotropic, and dromotropic effects mediated via parasympathetic ganglia in the dog heart," Am J Physiol Heart Circ Physiol 279: H1201-H1207 (2000).

Wijffels MC et al., "Atrial fibrillation begets atrial fibrillation," Circulation 92:1954-1968 (1995).

Sweeney JD et al., "An asymmetric two electrode cuff for generation of unidirectionally propagated action potentials," IEEE Transactions on Biomedical Engineering, vol. BME-33(6) (1986).

Ungar IJ et al., "Generation of unidirectionally propagating action potentials using a monopolar electrode cuff," Annals of Biomedical Engineering, 14:437-450 (1986).

van den Honert C et al., "A technique for collision block of peripheral nerve: Frequency dependence," MP-12, IEEE Trans. Biomed. Eng. 28:379-382 (1981).

van den Honert C et al., "Generation of unidirectionally propagated action potentials in a peripheral nerve by brief stimuli," Science, 206:1311-1312 (1979).

Randall WC ed., Neural Regulation of the Heart, Oxford University Press (1977), particularly pp. 100-106.

Rijkhoff NJ et al., "Orderly recruitment of motoneurons in an acute rabbit model," Ann. Conf. of the IEEE Eng., Medicine and Biology Soc., 20(5):2564 (1998).

Sweeney JD et al., "A nerve cuff technique for selective excitation of peripheral nerve trunk regions," IEEE Transactions on Biomedical Engineering, 37(7) (1990).

Martin PJ et al., "Phasic effects of repetitive vagal stimulation on atrial contraction," Circ. Res. 52(6):657-63 (1983).

Manfredi M, "Differential block of conduction of larger fibers in peripheral nerve by direct current," Arch. Ital. Biol., 108:52-71 (1970).

Wang H et al., "Nicotinic acetylcholine receptor alpha-7 subunit is an essential regulator of inflammation," Nature 421:384-388 (2003).

Waninger MS et al., "Electrophysiological control of ventricular rate during atrial fibrillation," PACE 23:1239-1244 (2000).

Vanoli E et al., "Vagal stimulation and prevention of sudden death in conscious dogs with a healed myocardial infarction," Circ Res 68(5):1471-81 (1991).

Veraart C et al., "Selective control of muscle activation with a multipolar nerve cuff electrode," IEEE Trans Biomed Eng, 40(7):640-53 (1993).

(56) References Cited

OTHER PUBLICATIONS

Li D et al., "Promotion of Atrial Fibrillation by Heart Failure in Dogs: Atrial Remodeling of a Different Sort," Circulation 100(1):87-95 (1999).
Morady F et al., "Effects of resting vagal tone on accessory atrioventricular connections," Circulation 81(1): 86-90 (1990).
Mushahwar VK et al., "Muscle recruitment through electrical stimulation of the lumbo-sacral spinal cord," IEEE Trans Rehabil Eng, 8(1):22-9 (2000).
Rijkhoff NJ et al., "Acute animal studies on the use of anodal block to reduce urethral resistance in sacral root stimulation," IEEE Transactions on Rehabilitation Engineering, 2(2):92 (1994).
Stramba-Badiale M et al., "Sympathetic-Parasympathetic Interaction and Accentuated Antagonism in Conscious Dogs," American Journal of Physiology 260 (2Pt 2):H335-340 (1991).
Kamath et al., in "Effect of vagal nerve electrostimulation on the power spectrum of heart rate variability in man," Pacing Clin Electrophysiol 15:235-43 (1992).
Kwan H et al., "Cardiovascular adverse drug reactions during initiation of antiarrhythmic therapy for atrial fibrillation," Can J Hosp Pharm 54:10-14 (2001).
Garrigue S et al., "Post-ganglionic vagal stimulation of the atrioventricular node reduces ventricular rate during atrial fibrillation," PACE 21(4), 878 (Part II) (1998).
Goodall EV et al., "Position-selective activation of peripheral nerve fibers with a cuff electrode," IEEE Trans Biomed Eng, 43(8):851-6 (1996).
Grill WM et al., "Inversion of the current-distance relationship by transient depolarization," IEEE Trans Biomed Eng, 44(1):1-9 (1997).
Higgins CB, "Parasympathetic control of the heart," Pharmacol. Rev. 25:120-155 (1973).
Jidéus L, "Atrial fibrillation after coronary artery bypass surgery: A study of causes and risk factors," Acta Universitatis Upsaliensis, Uppsala, Sweden (2001).
Jones, JFX et al., "Heart rate responses to selective stimulation of cardiac vagal C fibres in anaesthetized cats, rats and rabbits," J Physiol 489 (Pt 1):203-14 (1995).
Akselrod S et al., "Power spectrum analysis of heart rate fluctuation: a quantitative probe of beat-to-beat cardiovascular control," Science 213: 220-222 (1981).
Billette J et al., "Roles of the AV junction in determining the ventricular response to atrial fibrillation," Can J Physiol Pharamacol 53(4)575-85 (1975).
Borovikova LV et al., "Vagus nerve stimulation attenuates the systemic inflammatory response to endotoxin," Nature 405(6785):458-62 (2000).
De Ferrari GM, "Vagal reflexes and survival during acute myocardial ischemia in conscious dogs with healed myocardial infarction," Am J Physiol 261(1 Pt 2):H63-9 (1991).
van den Honert C et al., "A technique for collision block of peripheral nerve: Frequency dependence," MP-12, IEEE Trans. Biomed. Eng. 28:373-378 (1981).
Hoffer JA et al., "How to use nerve cuffs to stimulate, record or modulate neural activity", in Neural Prostheses for Restoration of Sensory and Motor Function, Chapin JK et al (Eds.), CRC Press (1st edition, 2000).
Lertmanorat Z et al., "A novel electrode array for diameter-dependent control of axonal excitability: a simulation study", IEEE Transactions on Biomedical Engineering 51(7): 1242-1250 (2004).
An Office Action dated Oct. 24, 2008, which issued during the prosecution of Applicant's U.S. Appl. No. 11/022,011.
A Supplementary European Search Report dated Nov. 4, 2009, which issued during the prosecution of Applicant's European Patent Application No. EP 03 72 3040.
A European Search Report dated Aug. 27, 2009, which issued during the prosecution of Applicant's European Patent Application No. EP 09 25 1749.
An Office Action dated Dec. 8, 2009, which issued during the prosecution of Applicant's U.S. Appl. No. 11/347,120.
An Office Action dated Jan. 21, 211, which issued during the prosecution of Applicant's U.S. Appl. No. 12/589,132.
An Examination Report dated Feb. 7, 2011, which issued during the prosecution of Applicant's European Patent Application No. 03725560.
A Supplementary European Search Report dated Aug. 16, 2010, which issued during the prosecution of Applicant's European Patent Application No. 03725560.
An Official Action dated May 26, 2011, which issued during the prosecution of Applicant's U.S. Appl. No. 12/012,366.
An Official Action dated May 23, 2011, which issued during the prosecution of Applicant's U.S. Appl. No. 11/978,776.
An Official Action dated Jun. 7, 2011, which issued during the prosecution of Applicant's U.S. Appl. No. 12/589,132.
An Extended European Search Report dated Jun. 6, 2011, which issued during the prosecution of Applicant's European Patent Application No. 11002403.
An Office Action dated Nov. 21, 2012, which issued during the prosecution of U.S. Appl. No. 12/952,058.
An International Search Report and a Written Opinion both dated Jul. 11, 2013, which issued during the prosecution of Applicant's PCT/IL2013/050286.

FIG. 2

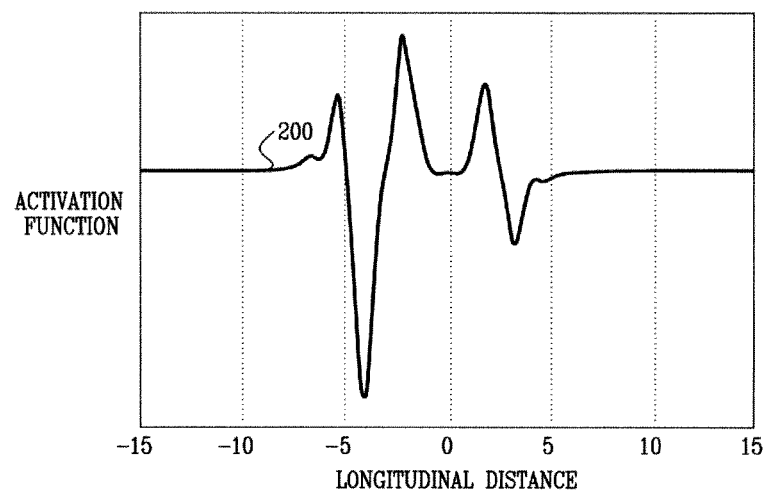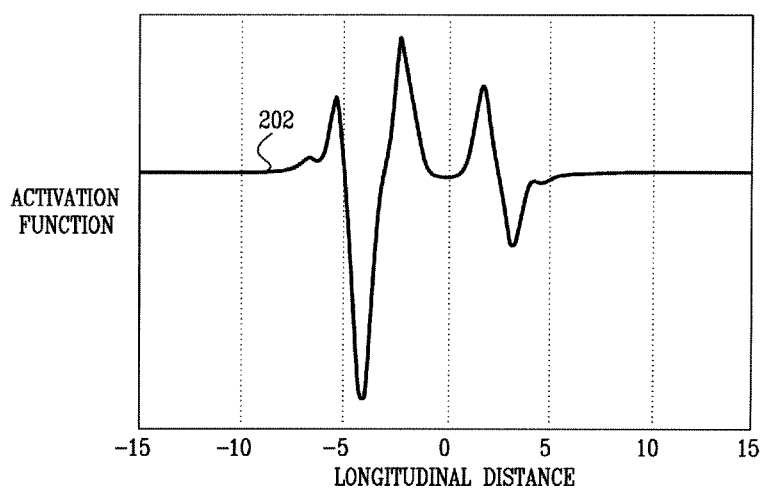

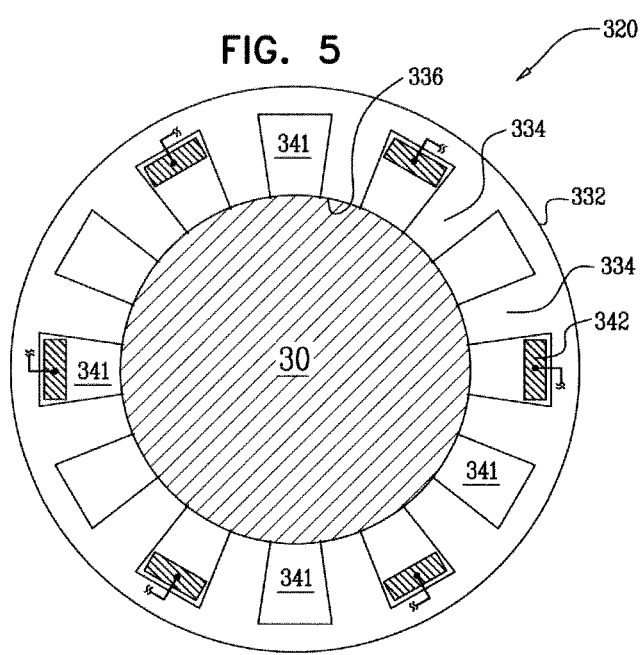

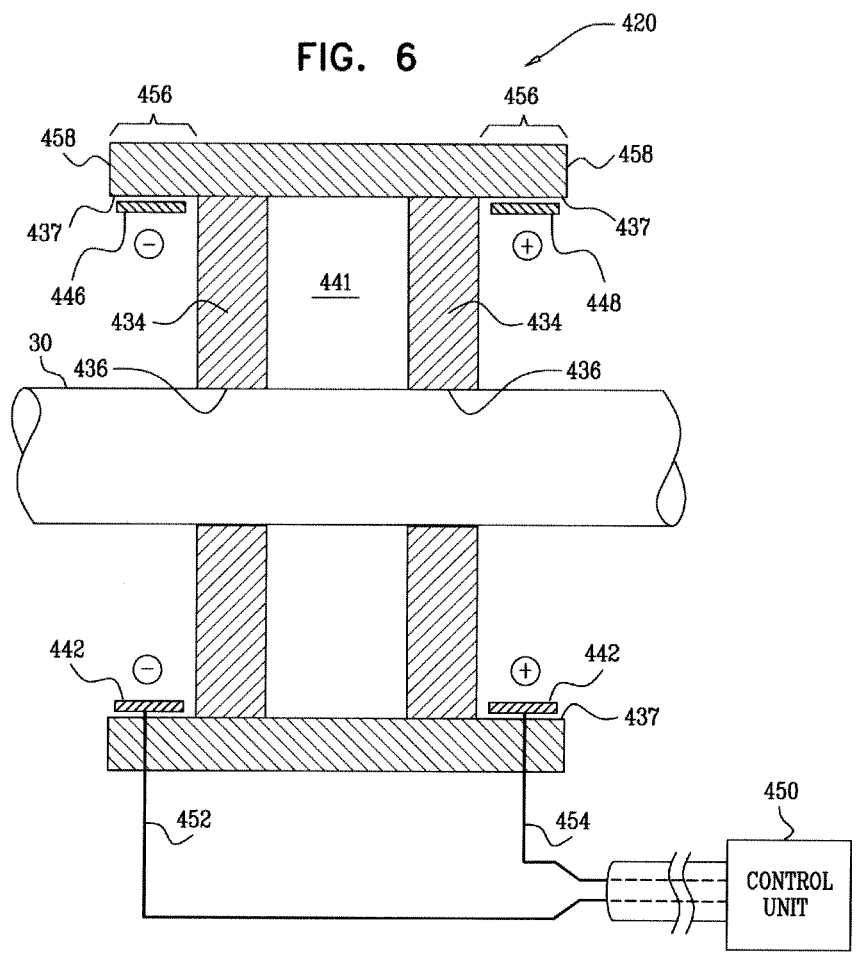

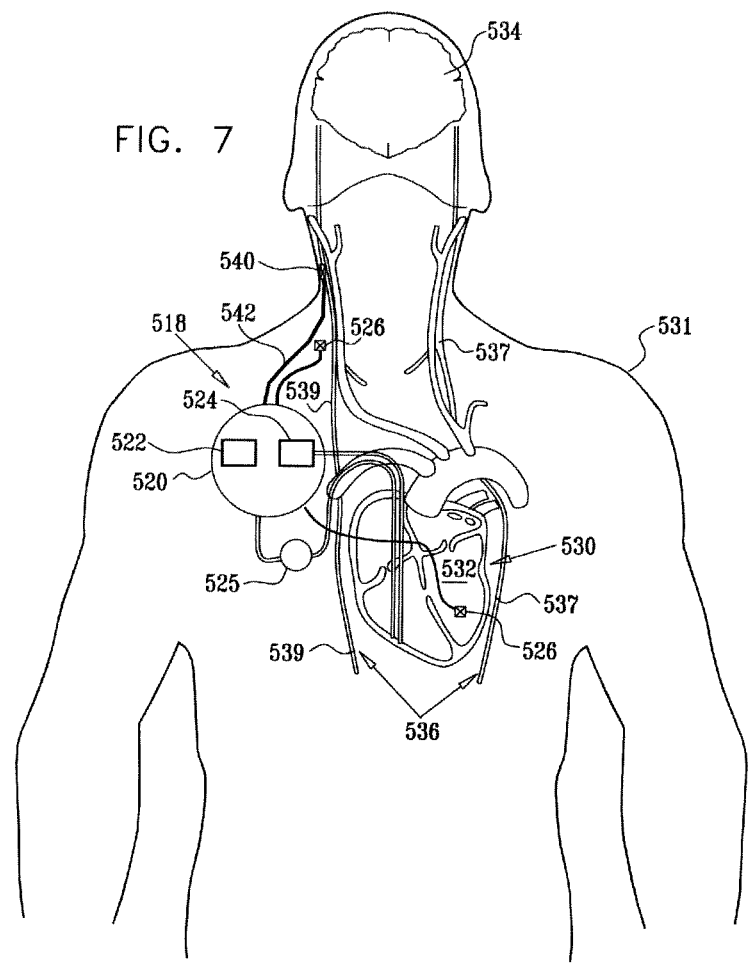

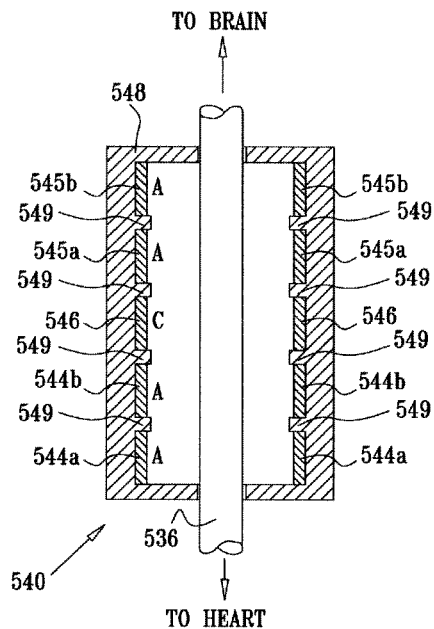
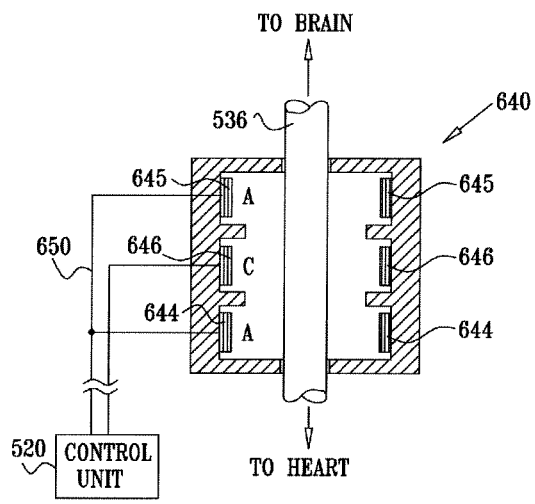

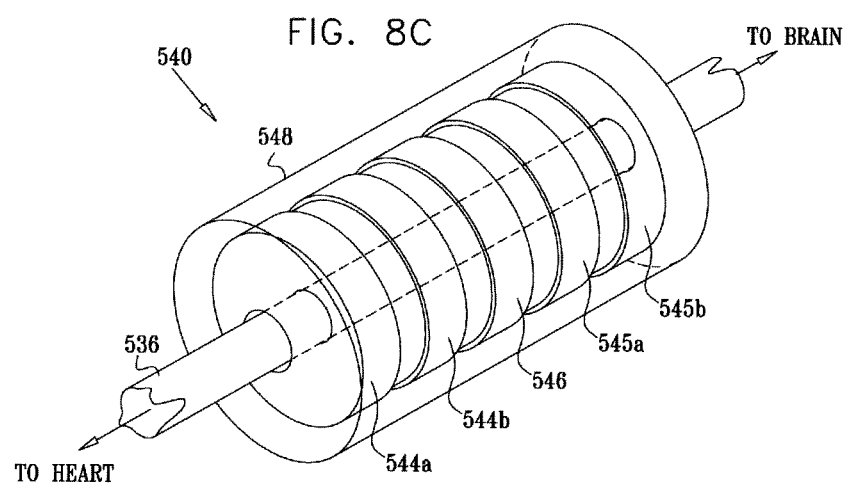

ELECTRODE CUFFS

CROSS-REFERENCE TO RELATED APPLICATIONS

The present application is a continuation-in-part of (a) U.S. application Ser. No. 12/217,930, filed Jul. 9, 2008, now abandoned, and (b) U.S. application Ser. No. 11/070,842, filed Feb. 24, 2005, now U.S. Pat. No. 8,386,056, which is a continuation of U.S. application Ser. No. 10/719,659, filed Nov. 20, 2003, now U.S. Pat. No. 7,778,711, which is a continuation-in-part of International Application PCT/IL03/00431, filed May 23, 2003. All of these applications are assigned to the assignee of the present application and are incorporated herein by reference.

FIELD OF THE INVENTION

The present invention relates generally to electrical stimulation of tissue, and specifically to methods and devices for regulating the stimulation of nerves.

BACKGROUND OF THE INVENTION

A number of patents and articles describe methods and devices for stimulating nerves to achieve a desired effect. Often these techniques include a design for an electrode or electrode cuff.

US Patent Application Publication 2010/0010603 to Ben-David et al., which is assigned to the assignee of the present application and is incorporated herein by reference, describes apparatus for application to a nerve of a subject. The apparatus includes a housing, which is configured to be placed at least partially around the nerve so as to define an inner surface of the housing that faces the nerve. A plurality of insulating elements are coupled to the inner surface of the housing at respective insulating element longitudinal positions along the housing, such that the inner surface of the housing and pairs of the insulating elements define one or more respective cavities at respective cavity longitudinal positions along the housing. One or more electrodes are fixed to the housing in fewer than all of the cavities. Other embodiments are also described.

PCT Publication WO 03/099377 to Ayal et al., which is assigned to the assignee of the present application and is incorporated herein by reference, describes apparatus for treating a subject, which includes an electrode device, adapted to be coupled to a vagus nerve of the subject, and a heart rate sensor, configured to detect a heart rate of the subject, and to generate a heart rate signal responsive thereto. The apparatus also includes a control unit, adapted to receive the heart rate signal, and, responsive to determining that the heart rate is greater than a threshold value, which threshold value is greater than a normal heart rate, drive the electrode device to apply a current to the vagus nerve, and configure the current so as to reduce the heart rate of the subject.

U.S. Pat. No. 6,907,295 to Gross et al., which is assigned to the assignee of the present application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

US Patent Application Publication 2006/0106441 to Ayal et al., which is assigned to the assignee of the present application and is incorporated herein by reference, describes apparatus for applying current to a nerve, including a housing, adapted to be placed in a vicinity of the nerve, and at least one cathode and at least one anode, fixed to the housing. The apparatus further includes two or more passive electrodes, fixed to the housing, and a conducting element, which electrically couples the passive electrodes to one another.

U.S. Pat. No. 4,608,985 to Crish et al. and U.S. Pat. No. 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode.

U.S. Pat. No. 5,824,027 Hoffer et al., which is incorporated herein by reference, describes a nerve cuff having one or more sets of electrodes for selectively recording electrical activity in a nerve or for selectively stimulating regions of the nerve. Each set of electrodes is located in a longitudinally-extending chamber between a pair of longitudinal ridges which project into the bore of the nerve cuff. The ridges are electrically insulating and serve to improve the selectivity of the nerve cuff. The ridges seal against an outer surface of the nerve without penetrating the nerve. In an embodiment, circumferential end sealing ridges extend around the bore at each end of the longitudinal ridges, and are described as enhancing the electrical and/or fluid isolation between different ones of the longitudinally-extending chambers.

U.S. Pat. No. 4,628,942 to Sweeney et al., which is incorporated herein by reference, describes an annular electrode cuff positioned around a nerve trunk for imposing electrical signals on to the nerve trunk for the purpose of generating unidirectionally propagated action potentials. The electrode cuff includes an annular cathode having a circular passage therethrough of a first diameter. An annular anode has a larger circular passage therethrough of a second diameter, which second diameter is about 1.2 to 3.0 times the first diameter. A non-conductive sheath extends around the anode, cathode, and nerve trunk. The anode and cathode are placed asymmetrically to one side of the non-conductive sheath.

As defined by Rattay, in an article entitled, "Analysis of models for extracellular fiber stimulation," IEEE Transactions on Biomedical Engineering, Vol. 36, no. 2, p. 676 (1989), which is incorporated herein by reference, the activation function (AF) of an unmyelinated axon is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, σ is the conductance tensor specifying the conductance of the various materials (electrode housing, axon, intracellular fluid, etc.), and j is a scalar function representing the current source density specifying the locations of current injection. The activation function is found by solving this partial differential equation for U. If an unmyelinated axon is defined to lie in the z direction, then the activation function is:

$$AF = \frac{\partial^2 U}{\partial z^2}.$$

In a simple, illustrative example of a point electrode located a distance d from the axis of an axon in a uniformly-conducting medium with conductance σ, the two equations above are solvable analytically, to yield:

$$AF = \frac{I_{el}}{4\pi\sigma} \cdot \frac{2z^2 - d^2}{(z^2 + d^2)^{2.5}},$$

where $I_{el}$ is the electrode current. It is seen that when σ and d are held constant, and for a constant positive $I_{el}$ (to correspond to anodal current), the minimum value of the activation function is negative, and is attained at z=0, i.e., at the point on the nerve closest to the source of the anodal current. Thus, the most negative point on the activation function corresponds to the place on a nerve where hyperpolarization is maximized, namely at the point on the nerve closest to the anode.

Additionally, this equation predicts positive "lobes" for the activation function on either side of z=0, these positive lobes peaking in their values at a distance which is dependent on each of the other parameters in the equation. The positive values of the activation function correspond to areas of depolarization, a phenomenon typically associated with cathodic current, not anodal current. However, it has been shown that excess anodal current does indeed cause the generation of action potentials adjacent to the point on a nerve corresponding to z=0, and this phenomenon is therefore called the "virtual cathode effect." (An analogous, but reverse phenomenon, the "virtual anode effect" exists responsive to excess cathodic stimulation.)

The Rattay article also describes techniques for calculating the activation function for nerves containing myelinated axons. The activation function in this case varies as a function of the diameter of the axon in question. Thus, the activation function calculated for a 1 micron diameter myelinated axon is different from the activation function calculated for a 10 micron diameter axon.

The following patents, which are incorporated herein by reference, may be of interest:

U.S. Pat. No. 6,684,105 to Cohen et al.
U.S. Pat. No. 5,423,872 to Cigaina
U.S. Pat. No. 4,573,481 to Bullara
U.S. Pat. No. 6,230,061 to Hartung
U.S. Pat. No. 5,282,468 to Klepinski
U.S. Pat. No. 4,535,785 to van den Honert et al.
U.S. Pat. No. 5,215,086 to Terry et al.
U.S. Pat. No. 6,341,236 to Osorio et al.
U.S. Pat. No. 5,487,756 to Kallesoe et al.
U.S. Pat. No. 5,634,462 to Tyler et al.
U.S. Pat. No. 6,456,866 to Tyler et al.
U.S. Pat. No. 4,602,624 to Naples et al.
U.S. Pat. No. 6,600,956 to Maschino et al.
U.S. Pat. No. 5,199,430 to Fang et al.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney JD et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed, Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92-99 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Hoffer J A at al., "How to use nerve cuffs to stimulate, record or modulate neural activity," in *Neural Prostheses for Restoration of Sensory and Motor Function*, Chapin J K et al. (Eds.), CRC Press (1st edition, 2000)

Jones J F at al., "Heart rate responses to selective stimulation of cardiac vagal C fibres in anaesthetized cats, rats and rabbits," J Physiol 489(Pt 1):203-14 (1995)

Evans M S et al., "Intraoperative human vagus nerve compound action potentials," Acta Neural Scand 110:232-238 (2004)

Fitzpatrick et al., "A nerve cuff design for the selective activation and blocking of myelinated nerve fibers," Ann. Conf. of the IEEE Eng. in Medicine and Biology Soc, 13(2), 906 (1991)

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J at al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using cuff electrodes to selectively excite peripheral nerve fibers distant from an electrode without exciting nerve fibers close to the electrode:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

Lertmanorat Z at al., "A novel electrode array for diameter-dependent control of axonal excitability: a simulation study," IEEE Transactions on Biomedical Engineering 51(7):1242-1250 (2004)

SUMMARY OF THE INVENTION

In embodiments of the present invention, an electrode cuff for applying current to a nerve comprises a housing, which is configured to placed at least partially around the nerve, and a plurality of insulating elements arranged at respective longitudinal positions along the housing such that an inner surface of the housing and pairs of the insulating elements define respective cavities (i.e., spaces surrounded by portions of the cuff) at respective longitudinal positions along the housing. The cuff further comprises one or more electrodes, fixed to the housing in fewer than all of the cavities. In other words, at least one of the cavities defined by a pair of the insulating elements does not have an electrode positioned therein. The electrode cuff is typically configured such that, after placement of the cuff, respective contact surfaces of the insulating elements at least partially come in physical contact with the nerve, or substantially in physical contact with the nerve, e.g., are less than about 0.5 mm from the surface of the nerve. As used in the present application, including in the claims, an "electrode" is an electrically conductive element that includes at least one surface that is not electrically insulated.

Providing the one or more empty cavities results in less physical contact between the contact surfaces of the insulating elements and the nerve for a cuff of a given length, than in a cuff of the same length without such an empty cavity. As a result, providing the empty cavities tends to reduce constriction of the nerve by the cuff, which may reduce side-effects of application of the cuff to the nerve. Providing the empty cavity does not have a material impact on the activation function achieved by the electrode cuff.

For some applications, providing a cuff having an increased length along the nerve is desirable, e.g., because such an increased length provides greater space for a distribution of electrodes that enables achievement of a desired activation function that could not be achieved with a shorter cuff. Providing the empty cavity enables the lengthening of the cuff without a concomitant increase in insulating element contact surface area.

There is therefore provided, in accordance with an embodiment of the present invention, apparatus for application to a nerve of a subject, including an electrode cuff, which includes:

a housing, configured to be placed at least partially around the nerve so as to define an inner surface of the housing that faces the nerve;

a plurality of insulating elements coupled to the inner surface of the housing at respective insulating element longitudinal positions along the housing, such that the inner surface of the housing and pairs of the insulating elements define one or more respective cavities at respective cavity longitudinal positions along the housing; and one or more electrodes, fixed to the housing in fewer than all of the cavities, such that at least one of the cavities is an empty cavity that does not have an electrode positioned therein.

For some applications, the apparatus further includes a control unit, coupled to the electrodes, and configured to drive at least a portion of the electrodes to apply a current to the nerve. For some applications, the electrodes include two or more cathode electrodes, and the empty cavity is between and directly adjacent along the cuff to two cavities containing two respective ones of the cathode electrodes. For some applications, the electrodes include two or more anode electrodes, and the empty cavity is between and directly adjacent along the cuff to two cavities containing two respective ones of the anode electrodes. For some applications, the electrodes include two or more cathode electrodes and one or more anode electrodes, and the empty cavity is between and directly adjacent along the cuff to two cavities containing two respective ones of the cathode electrodes. For some applications, the electrodes include two or more anode electrodes and one or more cathode electrodes, and the empty cavity is between and directly adjacent along the cuff to two cavities containing two respective ones of the anode electrodes. For some applications, the plurality of electrodes includes at least one cathode electrode, at least one anode electrode, and two or more passive electrodes, and the apparatus further includes a conducting element, which electrically couples the passive electrodes to one another.

For some applications, the plurality of insulating elements includes at least seven insulating elements, which are arranged along the housing such that the inner surface of the housing and the pairs of insulating elements define first, second, third, fourth, fifth, and sixth cavities, the first cavity closest to an end of the housing, the second adjacent to the first, the third adjacent to the second, the fourth adjacent to the third, the fifth adjacent to the fourth, and the sixth adjacent to the fifth, the at least one cathode electrode includes at least one first cathode electrode and at least one second cathode electrode, at least a first one of the passive electrodes is fixed to the housing in the first cavity, the at least one anode electrode is fixed to the housing in the second cavity, the at least one first cathode electrode is fixed to the housing in the third cavity, no electrodes are fixed to the housing in the fourth cavity, the at least one second cathode electrode is fixed to the housing in the fifth cavity, and at least a second one of the passive electrodes is fixed to the housing in the sixth cavity.

For some applications, the insulating elements are shaped so as to define respective contact surfaces, and the housing and the insulating elements are configured such that the contact surfaces are suitable for being positioned less than 0.5 mm from a surface of the nerve when the housing is placed at least partially around the nerve.

For some applications, the insulating elements are shaped so as to define respective contact surfaces, and the housing and the insulating elements are configured such that the contact surfaces are suitable for at least partially coming in physical contact with the nerve when the housing is placed at least partially around the nerve.

For some applications, a length that at least one of the insulating elements protrudes from the housing toward a central axis of the cuff is at least 0.5 mm.

For some applications, the electrodes are fixed to the housing in a number of the cavities, and a difference between the number of the cavities and a total number of the cavities is an integer between 1 and 3, inclusive, such that between 1 and 3 of the cavities do not have any of the electrodes fixed therein.

For some applications, the housing has a length of between 10 mm and 14 mm, an outer radius of between 4 mm and 8 mm, an inner radius of between 3 mm and 6 mm; the insulating elements have an outer radius of between 3 mm and 6 mm, and an inner radius of between 2 mm and 3.5 mm; and the plurality of insulating elements includes exactly seven insulating elements, respective edges of which are positioned within the housing at the following respective distances from one end of the housing: 0.0 mm, between 1.3 and 1.7 mm, between 2.7 and 3.3 mm, between 5.1 and 6.3 mm, between 7.1 and 8.7 mm, between 8.5 and 10.3 mm, and between 10.2 and 12.4 mm, and the insulating elements having the following respective widths: between 0.7 and 0.9 mm, between 0.7 and 0.9 mm, between 1.4 and 1.8 mm, between 0.7 and 0.9 mm, between 0.7 and 0.9 mm, between 1.1 and 1.3 mm, and between 0.7 and 0.9 mm.

For some applications, at least two of the electrodes are fixed to the housing in one of the cavities.

For some applications, the electrodes include ring electrodes.

For some applications, the electrodes are fixed to the housing in none of the one or more cavities, such that all of the one or more cavities are empty of electrodes.

For some applications, the one or more cavities include at least three cavities, and the electrodes are fixed to the housing in at least two of the cavities. For some applications, the one or more cavities include at least four cavities, and the electrodes are fixed to the housing in at least three of the cavities.

There is further provided, in accordance with an application of the present invention, apparatus for application to a nerve, including:

a cuff shaped so as to define along a longitudinal axis thereof one or more cavities open to the nerve when the cuff is placed at least partially around the nerve; and one or more electrodes, fixed to the cuff in fewer than all of the cavities, such that at least one of the cavities is an empty cavity that does not have an electrode positioned therein.

For some applications, the electrodes include ring electrodes.

For some applications, at least two of the electrodes are fixed to the cuff in one of the cavities.

For some applications, the electrodes are fixed to the cuff in none of the one or more cavities, such that all of the one or more cavities are empty of electrodes.

For some applications, the apparatus further includes a control unit, coupled to the electrodes, and configured to drive at least a portion of the electrodes to apply a current to the nerve. For some applications, the electrodes include two or more cathode electrodes, and the empty cavity is between and directly adjacent along the cuff to two cavities containing two respective ones of the cathode electrodes. For some applications, the electrodes include two or more anode electrodes, and the empty cavity is between and directly adjacent along the cuff to two cavities containing two respective ones of the anode electrodes. For some applications, the electrodes include two or more cathode electrodes and one or more anode electrodes, and the empty cavity is between and directly adjacent along the cuff to two cavities containing two respective ones of the cathode electrodes. For some applications, the electrodes include two or more anode electrodes and one or more cathode electrodes, and the empty cavity is between and directly adjacent along the cuff to two cavities containing two respective ones of the anode electrodes.

There is still further provided, in accordance with an application of the present invention, a method including:

placing, at least partially around a nerve, a cuff shaped so to define along a longitudinal axis thereof one or more cavities open to the nerve, the cuff including one or more electrodes fixed to the cuff in few than all of the cavities, such that at least one of the cavities is an empty cavity that does not have an electrode positioned therein; and applying a current to the nerve using at least a portion of the electrodes.

The present invention will be more fully understood from the following detailed description of embodiments thereof, taken together with the drawings, in which:

BRIEF DESCRIPTION OF THE DRAWINGS

FIG. 2 is a schematic, cross-sectional illustration of another electrode cuff for applying current to a nerve, in accordance with an embodiment of the present invention;

FIGS. 3 and 4 are graphs modeling calculated activation functions, respectively, when current is applied using electrode cuffs similar to those shown in FIGS. 1 and 2, respectively, in accordance with an embodiment of the present invention;

FIG. 5 is a schematic, longitudinal cross-sectional view of another electrode cuff for applying current to a nerve, in accordance with an embodiment of the present invention;

FIG. 6 is a schematic, cross-sectional illustration of yet another electrode cuff for applying current to a nerve, in accordance with an embodiment of the present invention;

FIG. 7 is a block diagram that schematically illustrates a vagal stimulation system applied to a vagus nerve of a patient, in accordance with an embodiment of the present invention;

FIG. 8A is a simplified cross-sectional illustration of a multipolar electrode device applied to a vagus nerve, in accordance with an embodiment of the present invention;

FIG. 8B is a simplified cross-sectional illustration of a generally-cylindrical electrode device applied to a vagus nerve, in accordance with an embodiment of the present invention; and FIG. 8C is a simplified perspective illustration of the electrode device of FIG. 8A, in accordance with an embodiment of the present invention.

DETAILED DESCRIPTION OF EMBODIMENTS

Figure 1:
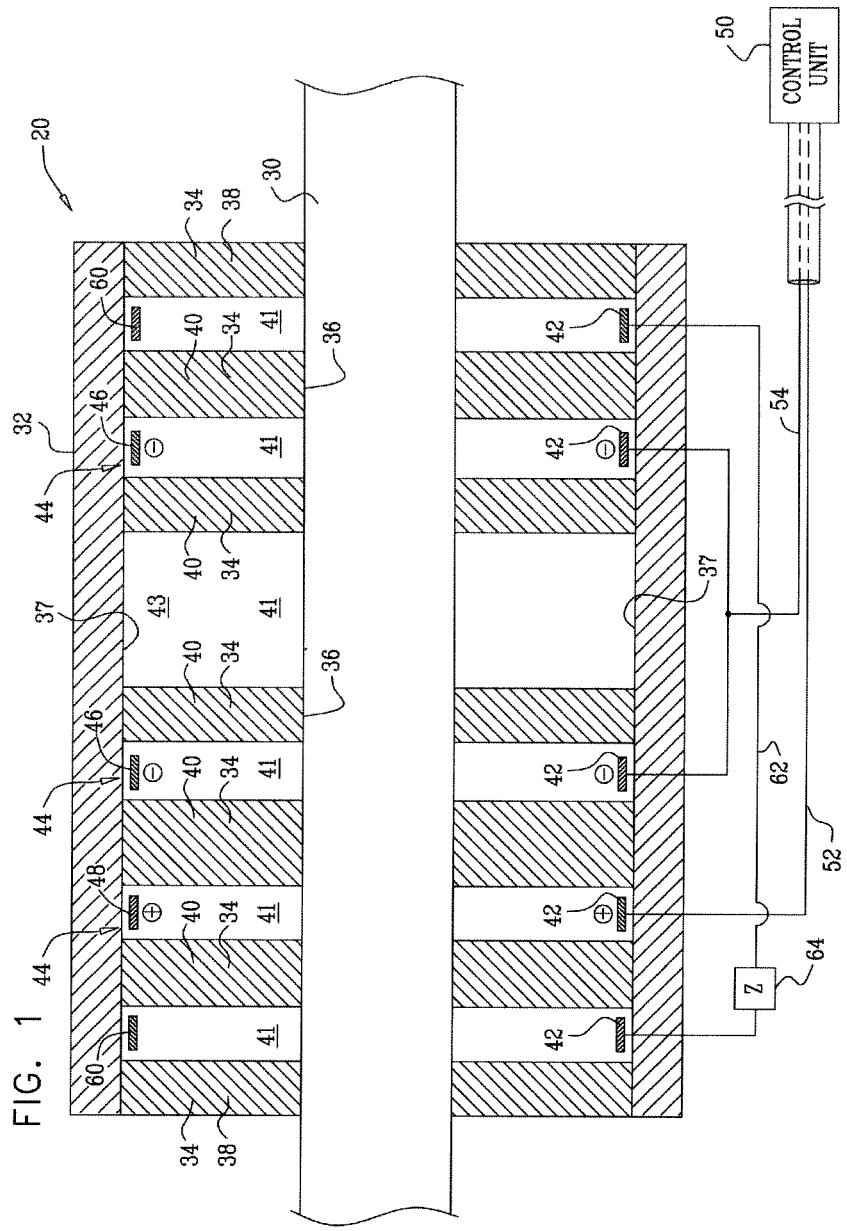
FIG. 1 is schematic, cross-sectional illustration of an electrode cuff for applying current to a nerve, in accordance with respective embodiments of the present invention.

FIG. 1 is a schematic, cross-sectional illustration of an electrode cuff 20 for applying current to a nerve 30, in accordance with an embodiment of the present invention. Electrode cuff 20 comprises a housing 32 which defines an outer surface of the cuff when the cuff is placed at least partially around nerve 30. Housing 32 typically comprises an elastic, electrically-insulating material such as silicone or polyurethane, which may have, for example, a Shore A of between about 35 and about 70, such as about 40.

Electrode cuff 20 further comprises a plurality of insulating elements 34 that are arranged at respective positions along the housing, and are typically fixed to an inner surface 37 of housing 32 that faces nerve 30 when the electrode cuff is placed at least partially around the nerve. Insulating elements 34 typically comprise an elastic, electrically-insulating material such as silicone or silicone copolymer, which, for some applications, is softer than that of housing 32, for example, a Shore A of between about 10 and about 30, such as about 10. Electrode cuff 20 is typically configured such that, after placement of the cuff on the nerve, respective contact surfaces 36 of insulating elements 34 at least partially come in physical contact with the nerve, or substantially in physical contact with the nerve, e.g., are less than about 0.5 mm from the surface of the nerve. For some applications, a length that at least one of insulating elements 34 protrudes from housing 32 toward nerve 30 is at least 0.5 mm, such as at least 1 mm. For some applications, insulating elements 34 and housing 32 are constructed as separate elements that are coupled to one another, while for other applications, the insulating elements and housing are constructed as a single integrated element that is shaped to define the insulating elements and housing.

Insulating elements 34 typically comprise one or more (such as exactly two) end insulating elements 38 arranged at or near respective ends of the cuff, and two or more internal insulating elements 40 arranged at respective positions along the cuff between the end insulating elements. End insulating elements 38 extend along nerve 30 in order to electrically isolate a portion of the nerve within electrode cuff 20 from a portion of the nerve outside the electrode cuff.

Inner surface 37 of housing 32 and pairs of insulating elements 34 define a respective cavities 41 along the housing. (It is noted that some pairs of the insulating elements may not define a cavity, such as if two or more of the insulating elements are arranged in contact with one another.)

Electrode cuff 20 comprises a plurality of electrodes 42, fixed within housing 32 in respective cavities 41 defined by respective pairs insulating elements 34 and inner surface 37 of housing 32. At least one of cavities 41 defined by a pair of the insulating elements does not have an electrode positioned therein. For example, in the embodiment shown in FIG. 1, the insulating elements define six cavities 41, a fourth one 43 of which (counting from the left in the figure) does not have an electrode positioned therein. For some applications, at least two, such as least three, of the cavities do not have electrodes positioned therein. Electrodes 42 are typically fixed to inner surface 37 of housing 32. For some applications, none of the cavities have electrodes positioned therein (see, for example, FIG. 6).

For some applications, at least one of the empty cavities has a length along the cuff of at least 0.5 mm, such as at least 0.7 mm, e.g., at least 1.4 mm or at least 2 mm, and/or no more than 5 mm, e.g., no more than 2 mm. For some applications, a length along the cuff of one of the empty cavities is between about 0.5 and about 5 times a length of one of the cavities that has an electrode therein, such as between about 1 and about 2 times the length.

For some applications, at least one of the empty cavities is directly adjacent along the cuff to two cavities containing an anode electrode and a cathode electrode, respectively. For some applications, at least one of the empty cavities is directly adjacent along the cuff to two cavities containing two respective anode electrodes, or to two cavities containing two respective cathode electrodes. Alternatively, at least one of the two endmost cavities is empty, e.g., one side of at least one of the empty cavities is defined by one of end insulating elements 38.

Providing the empty cavity results in less physical contact between contact surfaces 36 of insulating elements 34 and nerve 30 for a cuff of a given length, than in a cuff of the same length without such an empty cavity. As a result, providing the empty cavity tends to reduce constriction of the nerve by the cuff, which may reduce side-effects of application of the cuff to the nerve. Providing the empty cavity does not have a material impact on the activation function achieved by the electrode cuff, as described hereinbelow with reference to FIGS. 3 and 4.

Internal insulating elements 40 are arranged so as to electrically separate electrodes 42, and to guide current from one of the electrodes towards the nerve prior to being taken up by another one of the electrodes. Typically (as shown), insulating elements 34 are closer to nerve 30 than are the electrodes, i.e., the electrodes are recessed within the cavities. Alternatively (not shown), insulating elements 34 are generally flush with the faces of the electrodes, such that the inner surfaces of insulating elements and the conductive surfaces of the electrode are equidistant from the nerve.

Electrodes 42 comprise at least one active, i.e., stimulating and/or sensing, electrode 44, such as one or more cathode electrodes 46, one or more anode electrodes 48, or at least one cathode electrode 46 and at least one anode electrode 48. Active electrodes 44 are coupled to an implantable or external control unit 50 by leads 52 and 54. For some applications, active electrode configurations and/or stimulation techniques are used which are described in one or more of the patent applications incorporated by reference hereinbelow. For some applications, two or more of the active electrodes are shorted to one another inside or outside of the cuff, such as shown for cathode electrodes 46 in FIG. 1.

In an embodiment of the present invention, electrode cuff 20 further comprises two or more passive electrodes 60, fixed within housing 32, and a conducting element 62, typically a wire, which electrically couples the passive electrodes to one another. A "passive electrode," as used in the present application including the claims, is an electrode that is electrically "device-coupled" to neither (a) any circuitry that is electrically device-coupled to any of the cathode electrodes or anode electrodes, nor (b) an energy source. "Device-coupled" means coupled, directly or indirectly, by components of a device, and excludes coupling via tissue of a subject. (It is noted that the passive electrodes may be passive because of a software-controlled setting of the electrode assembly, and that the software may intermittently change the setting such that these electrodes are not passive.) To "passively electrically couple," as used in the present application including the claims, means to couple using at least one passive electrode and no non-passive electrodes. Passive electrodes 60 and conducting element 62 create an additional electrical path for the current, such as an additional path for the current that would otherwise leak outside electrode cuff 20 and travel around the outside of the housing through tissue of the subject. For some applications, conducting element 62 comprises at least one passive element 64, such as a resistor, capacitor, and/or inductor. In this embodiment, end insulating elements 38 help direct any current that leaks from active electrodes 44 through the electrical path created by passive electrodes 60 and conducting element 62. For some applications, active electrodes 44 are positioned within housing 32 longitudinally between the two or more passive electrodes 60 (as shown in FIG. 1). Alternatively, at least one of the passive electrodes is positioned between the at least one cathode electrode and the at least one anode electrode (configuration not shown).

In an embodiment of the present invention, electrode cuff 20 comprises one or more passive electrodes 60 which are not electrically device-coupled to one another. For some applications, the electrode cuff comprises exactly one passive electrode 60. A separate conducting element, typically a wire, is coupled to each passive electrode at a first end of the conducting element. The second end of the conducting element terminates at a relatively-remote location in the body of the subject that is at a distance of at least 1 cm, e.g., at least 2 or 3 cm, from electrode cuff 20. The remote location in the body thus serves as a ground for the passive electrode. For some applications, an electrode is coupled to the remote end of the conducting element, so as to increase electrical contact with tissue at the remote location.

For some applications, housing 32 has a length of between about 10 and about 14 mm, e.g., about 12.1 mm; an outer radius of between about 4 and about 8 mm, e.g., about 5.9 mm; and an inner radius of between about 3 and about 6 mm, e.g., about 4.5 mm. For some applications, insulating elements 34 have an outer radius of between about 3 and about 6 mm, e.g., about 4.5 mm (the outer radius of the insulating elements is typically equal to the inner radius of the housing), and an inner radius of between about 2 and about 3.5 mm. For some applications in which cuff 20 comprises exactly two end insulating elements 38 and exactly five internal insulating elements 40, respective edges of insulating elements 34 are positioned within cuff 32 at the following distances from one end of the cuff: 0.0 mm, between 1.3 and 1.7 mm (e.g., 1.5 mm), between 2.7 and 3.3 mm (e.g., 3.0 mm), between 5.1 and 6.3 mm (e.g., 5.7 mm), between 7.1 and 8.7 mm (e.g., 7.9 mm), between 8.5 and 10.3 mm (e.g., 9.4 mm), and between 10.2 and 12.4 mm (e.g., 11.3 mm), and the insulating elements having the following respective widths: between 0.7 and 0.9 mm (e.g., 0.8 mm), between 0.7 and 0.9 mm (e.g., 0.8 mm), between 1.4 and 1.8 mm (e.g., 1.6 mm), between 0.7 and 0.9 mm (e.g., 0.8 mm), between 0.7 and 0.9 mm (e.g., 0.8 mm), between 1.1 and 1.3 mm (e.g., 1.2 mm), and between 0.7 and 0.9 mm (e.g., 0.8 mm). For some applications, electrodes 42 comprise Pt/Ir. For some applications, as shown in FIG. 1, electrodes 42 are shaped as rings (e.g., reference numeral 60 and leftmost reference numeral 42 in FIG. 1 refer to a single ring electrode). The rings may have an outer radius that equals, or is slightly greater or less than, the inner radius of housing 32.

In an embodiment of the present invention, at least some of the electrodes do not comprise ring electrodes. Instead, each of at least one of non-empty cavities 41 has fixed therein a plurality of electrodes positioned at least partially circumferentially around a central axis of the cuff. In other words, electrodes 42 are first electrodes 42, fixed within housing 32 in respective cavities 41, and cuff 20 comprises at least one second electrode 42, fixed within housing 32 in one of the cavities 41 in which one of the first electrodes 42 is fixed. For some applications, the plurality of electrodes within a single cavity are circumferentially separated from one another by one or more circumferentially arranged insulating elements.

In an embodiment of the present invention, at least one of the one or more of cavities 41 which are empty in the embodiments described hereinabove, instead has fixed therein one or more electrodes that are not electrically device-coupled (as defined hereinabove) to any elements of the device outside of the cavity. These electrodes thus do not serve the normal function of electrodes in an electrode cuff, i.e., conducting current to and/or from tissue.

In an embodiment of the present invention, nerve 30 is a vagus nerve, and electrode cuff 20 is configured to be placed at least partially around the vagus nerve such that anode electrode 48 is more proximal to the brain than are cathode electrodes 46.

Figure 2:
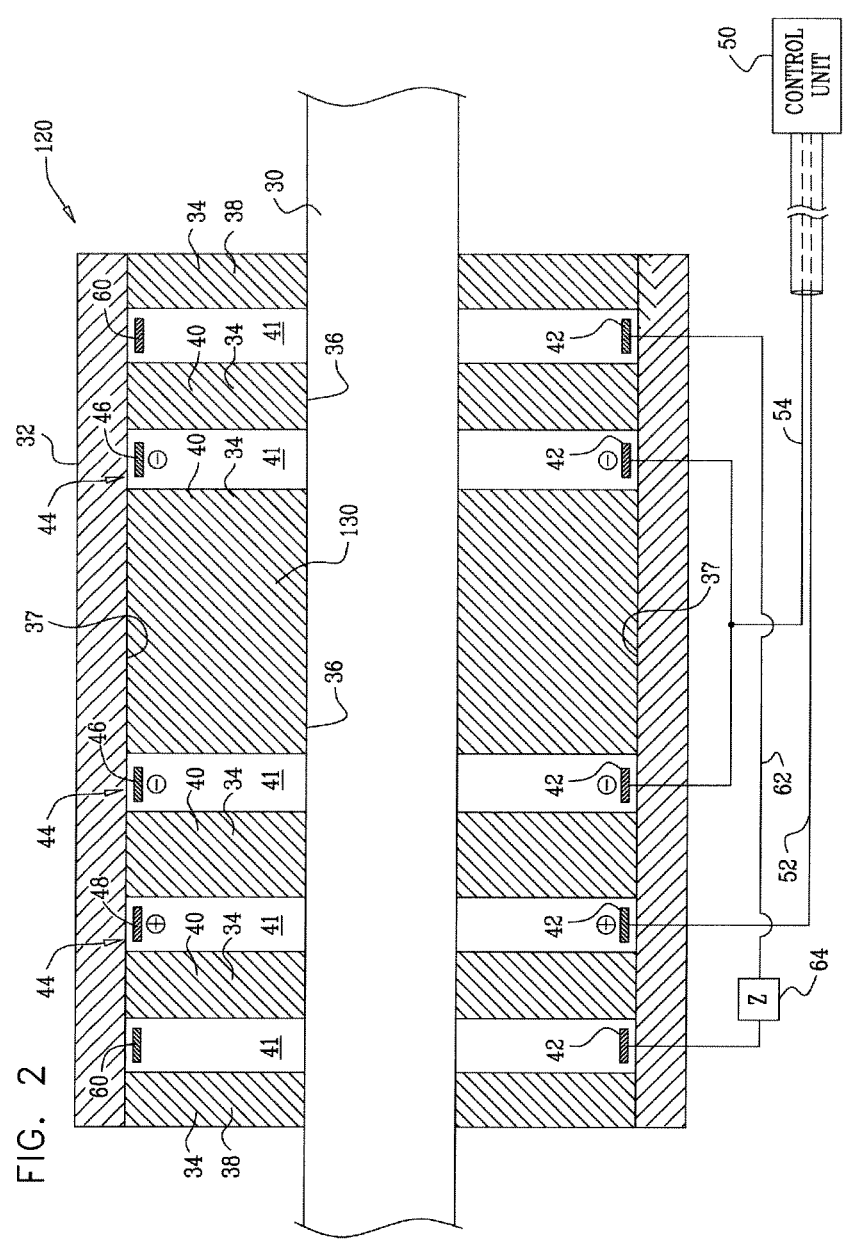

FIG. 2 is a schematic, cross-sectional illustration of an electrode cuff 120 for applying current to nerve 30, in accordance with an embodiment of the present invention. Electrode cuff 120 is identical to electrode cuff 20, described hereinabove with reference to FIG. 1, except that cuff 120 lacks cavity 43 of cuff 20, which, as mentioned above, does not have one of electrodes 42 positioned therein. Instead of the two internal insulating elements 40 that define cavity 43 in cuff 20, cuff 120 has a single, elongated insulating element 130, having a length along the housing equal to the sum of the lengths along the cuff of cavity 43 and the two internal insulating elements 40 that define cavity 43 in cuff 20.

Reference is made to FIGS. 3 and 4, which are graphs modeling calculated activation functions 200 and 202, respectively, when current is applied using electrode cuffs similar to those shown in FIGS. 1 and 2, respectively, in accordance with an embodiment of the present invention. These activation functions model myelinated nerve fibers having a diameter of 1 micrometer, over a portion of the length of nerve 30, at a radius of 1.2 mm from the axis of the nerve. For the purposes of modeling these activation functions, (a) two cathode electrodes 46 are placed at longitudinal sites on the nerve labeled $z=2.25$ mm and $z=-1.65$ mm, respectively, (b) anode electrode 48 is placed at a longitudinal site $z=-4.15$ mm, and (c) two passive electrodes 60 are placed at longitudinal sites $z=4.15$ mm and $z=-5.65$ mm, respectively. All of the electrodes are placed at a radius of $R=2.5$ mm from the axis of nerve 30, which has a radius of 1.35 mm. The cavity of activation function 200 (FIG. 3) is at $z=0.4$ mm. The inner surfaces of all of the insulating elements (i.e., the surfaces closest to the nerve) are placed at a radius $R=1.5$ mm from the axis of nerve 30.

A comparison of activation functions 200 and 202 shows that the two activation functions are nearly identical, which demonstrates that providing empty cavity 43 does not have a material impact on the activation function achieved by the electrode cuff.

For some applications, electrode cuff 20 is configured to selectively stimulate fibers of the nerve having certain diameters, such as by using techniques described in one or more of the patent applications incorporated by reference hereinbelow. For example, control unit 50 may drive cathode electrode 46 to apply to nerve 30 a stimulating current, which is capable of inducing action potentials in a first set and a second set of nerve fibers of the nerve, and drive anode electrode 48 to apply to the nerve an inhibiting current, which is capable of inhibiting the induced action potentials traveling in the second set of nerve fibers, the nerve fibers in the second set having generally larger diameters than the nerve fibers in the first set.

For some applications, electrode cuff 20 is configured to apply unidirectional stimulation to the nerve, such as by using techniques described in one or more of the patent applications incorporated by reference hereinbelow. For example, control unit 50 may drive anode electrode 48 to apply an inhibiting current capable of inhibiting device-induced action potentials traveling in a non-therapeutic direction in nerve 30. For some applications, electrode cuff 20 comprises primary and secondary anode electrodes, the primary anode electrode located between the secondary anode electrode and the cathode electrode. The secondary anode electrode is typically adapted to apply a current with an amplitude less than about one half an amplitude of a current applied by the primary anode electrode.

Reference is made to FIG. 5, which is a schematic, cross-sectional view of an electrode cuff 320 for applying current to nerve 30, in accordance with an embodiment of the present invention. Electrode cuff 320 comprises a housing 332 which defines an outer surface of the cuff when the cuff is placed at least partially around nerve 30. Housing 332 typically comprises an elastic, electrically-insulating material such as silicone or polyurethane, which may have, for example, a Shore A of between about 35 and about 70, such as about 40. Electrode cuff 20 further comprises a plurality of in insulating elements 334 which are arranged at respective circumferential positions around the housing, and which extend longitudinally along at least a portion of a length of the housing. Insulating elements 334 typically comprise an elastic, electrically-insulating material such as silicone or silicone copolymer, which, for some applications, is softer than that of housing 332, for example, a Shore A of between about 10 and about 30, such as about 10. Electrode cuff 320 is typically configured such that, after placement of the cuff on the nerve, respective contact surfaces 336 of insulating elements 334 come in physical contact with the nerve, or substantially in physical contact with the nerve, e.g., are less than about 0.5 mm from the surface of the nerve. For some applications, a length that at least one of insulating elements 334 protrudes from housing 332 toward nerve 330 is at least 0.5 mm, such as at least 1 mm. For some applications, insulating elements 334 and housing 332 are constructed as separate elements that are coupled to one another, while for other applications, the insulating elements and housing are constructed as a single integrated element that is shaped to define the insulating elements and housing.

Together, insulating elements 334 define a plurality of n cavities 341 around housing 332, wherein n is less than or equal to m (the number of insulating elements, as mentioned above). Typically, n equals m. Alternatively, n is less than m, such as if two or more of the insulating elements are arranged in contact with one another. It is noted that the cavities 341 of electrode cuff 320 are oriented in a direction that is generally perpendicular to that of cavities 41 of electrode cuff 20 of FIG. 1. Insulating elements 334 of electrode cuff 320 run along the nerve in a direction parallel with a longitudinal axis of the nerve, while insulating elements 34 of electrode cuff 20 surround all or a portion of the nerve.

Electrode cuff 320 comprises a plurality of p electrodes 342, fixed within housing 332 in respective cavities 341 defined by two of insulating elements 334, wherein p is less than n. In other words, at least one of cavities 341 defined by a pair of the insulating elements does not have an electrode positioned therein. For example, in the embodiment shown in FIG. 5, the insulating elements define twelve cavities 341, half of which do not have an electrode positioned therein. For some applications, p equals a fraction of n, such as ⅔, ½, ⅓, or ¼.

For some applications, electrode cuff 320 comprises elements described hereinabove with reference to FIG. 1, such active and/or passive electrodes, and/or a control unit coupled to the cuff with leads.

FIG. 6 is a schematic, cross-sectional illustration of an electrode cuff 420 for applying current to nerve 30, in accordance with an embodiment of the present invention. Electrode cuff 420 comprises a housing 432 which defines an outer surface of the cuff when the cuff is placed at least partially around nerve 30. Housing 432 typically comprises an elastic, electrically-insulating material such as silicone or polyurethane, which may have, for example, a Shore A of between about 35 and about 70, such as about 40.

Electrode cuff 420 further comprises at least two, e.g., exactly two, insulating elements 434 that are arranged at respective positions along the housing, and are typically fixed to an inner surface 437 of the housing that faces nerve 30 when the cuff is placed at least partially around the nerve. Insulating elements 434 typically comprise an elastic, electrically-insulating material such as silicone or silicone copolymer, which, for some applications, is softer than that of housing 432, for example, a Shore A of between about 10 and about 30, such as about 10. Electrode cuff 420 is typically configured such that, after placement of the cuff on the nerve, respective contact surfaces 436 of insulating elements 434 come in physical contact with the nerve, or substantially in physical contact with the nerve, e.g., are less than about 0.5 mm from the surface of the nerve. For some applications, a length that at least one of insulating elements 434 protrudes from housing 432 toward nerve 30 is at least 0.5 mm, such as at least 1 mm. For some applications, insulating elements 434 and housing 432 are constructed as separate elements that are coupled to one another, while for other applications, the insulating elements and housing are constructed as a single integrated element that is shaped to define the insulating elements and housing. Insulating elements 434 extend along nerve 30 in order to electrically isolate a portion of the nerve within electrode cuff 420 from a portion of the nerve outside the electrode cuff.

Insulating elements 434 are positioned along housing 432 such that end portions 456 of housing 432 extend beyond the insulating elements toward respective longitudinal ends 458 of the housing. In other words, the insulating elements are longitudinally recessed from ends 458 of the housing. In addition, insulating elements 434 are positioned along housing 432 such that inner surface 437 of housing 432 and one or more pairs of the insulating elements define one or more respective cavities 441 along the housing. In the exemplary configuration shown in FIG. 6, the inner surface of the housing and exactly one pair of the insulating elements define exactly one cavity.

Cuff 420 comprises at least two electrodes 442, each of which is fixed to inner surface 437 of housing 432 at at least a portion of one of end portions 456 of housing 432. At least one of cavities 441, e.g., all of cavities 441 and/or exactly one of the cavities, does not have an electrode positioned therein. In other words, the electrodes are fixed to the housing in fewer than all of the cavities, e.g., in none of the cavities. For some applications, at least one of the empty cavities has a length along the cuff of at least 0.5 mm, such as at least 0.7 mm, e.g., at least 1.4 mm or at least 2 mm, and/or no more than 5 mm, e.g., no more than 3 mm or no more than 3 cm.

Providing the empty cavity results in less physical contact between contact surfaces 436 of insulating elements 434 and nerve 30 for a cuff of a given length, than in a cuff of the same length without such an empty cavity. As a result, providing the empty cavity tends to reduce constriction of the nerve by the cuff, which may reduce side-effects of application of the cuff to the nerve. Providing the empty cavity does not have a material impact on the activation function achieved by the electrode cuff.

Electrodes 442 comprise at least one active, i.e., stimulating and/or sensing, electrode, such as at least one cathode electrode 446 and at least one anode electrode 448. The active electrodes are coupled to an implantable or external control unit 450 by leads 452 and 458. For some applications, active electrode configurations and/or stimulation techniques are used which are described in one or more of the patent applications incorporated by reference hereinbelow. For some applications, two or more of the active electrodes are shorted to one another inside or outside of the cuff, such as shown for cathode electrodes 46 in FIG. 1. For some applications, cuff 420 comprises one or more passive electrodes, as described hereinabove with reference to FIG. 1.

In an embodiment of the present invention, at least some of electrodes 442 comprise ring electrodes. Alternatively, the electrodes do not comprise ring electrodes. Instead, fixed to at least a portion of each of end portions are a plurality of electrodes positioned at least partially circumferentially around a central axis of the cuff. In other words, electrodes 442 are first electrodes 442, and cuff 420 comprises at least one second electrode 442. For some applications, the plurality of electrodes are circumferentially separated from one another by one or more circumferentially arranged insulating elements.

In an embodiment of the present invention, at least one of the one or more of cavities 441 which are empty in the embodiment described hereinabove, instead has fixed therein one or more electrodes that are not electrically device-coupled (as defined hereinabove) to any elements of the device outside of the cavity. These electrodes thus do not serve the normal function of electrodes in an electrode cuff, i.e., conducting current to and/or from tissue.

In an embodiment of the present invention, insulating elements 434 are not positioned so as to define any cavities 441. For example, insulating elements 434 may comprise exactly one insulating element, which may have a length of at least 0.5 mm, such as at least 1 mm.

It is noted that although electrode cuffs 20, 320 and 420 and their elements are generally shown in the figures and described herein in a cylindrical configuration, other geometrical configurations, such as non-rotationally symmetric configurations, are also suitable for applying the principles of the present invention. In particular, housings 32, 332 or 432 of the electrode cuffs (and the electrodes themselves) may form a complete circle around nerve 30, or they may define an arc between approximately 0 and 90 degrees, between 90 and 180 degrees, between 180 and 350 degrees, or between 350 and 359 degrees around the nerve. For some applications, electrode cuff 20 or 420 comprises electrodes that form rings around the nerve, such that housing 32 surrounds the electrodes.

In an embodiment of the present invention, techniques described herein are practiced in combination with techniques described with reference to FIGS. 2, 3, and/or 6 of U.S. patent application Ser. No. 11/280,884 to Ayal et al., filed Nov. 15, 2005, which published as US Patent Application Publication 2006/0106441, and which is assigned to the assignee of the present application and is incorporated herein by reference. For example:

- for some applications, a closest distance between cathode electrodes 46 (i.e., the distance between the respective cathode electrodes' edges that are closest to one another) is equal to at least a radius R of nerve 30, e.g., at least 1.5 times the radius of the nerve, as described with reference to FIG. 2 of the '441 publication; and/or
- for some applications, end insulating elements 38 are elongated, as described with reference to FIG. 6 of the '441 publication.

As used in the present patent application, including in the claims, "longitudinal" means along the length of, and does not mean "around" or "circumferential." For example, "longitudinal positions" along the housing means positions along the length of the housing, rather than positions arranged circumferentially around a longitudinal axis of the housing or the nerve. Such longitudinal positions might be measured in mm from one end of the housing.

FIG. 7 is a block diagram that schematically illustrates a vagal stimulation system 518 comprising a multipolar electrode device 540, in accordance with an embodiment of the present invention. Electrode device 540 is applied to a portion of a vagus nerve 536 (either a left vagus nerve 537 or a right vagus nerve 539), which innervates a heart 530 of a patient 531. Typically, system 518 is utilized for treating a heart condition such as heart failure and/or cardiac arrhythmia. Vagal stimulation system 518 further comprises an implanted or external control unit 520, which typically communicates with electrode device 540 over a set of leads 542. Control unit 520 drives electrode device 540 to (i) apply signals to induce the propagation of efferent nerve impulses towards heart 530, and (ii) suppress artificially-induced afferent nerve impulses towards a brain 534 of the patient, in order to minimize unintended side effects of the signal application. The efferent nerve pulses in vagus nerve 536 are induced by electrode device 540 in order to regulate the heart rate of the patient.

For some applications, control unit 520 is adapted to receive feedback from one or more of the electrodes in electrode device 540, and to regulate the signals applied to the electrode device responsive thereto.

Control unit 520 is typically adapted to receive and analyze one or more sensed physiological parameters or other parameters of the patient, such as heart rate, electrocardiogram (ECG), blood pressure, indicators of decreased cardiac contractility, cardiac output, norepinephrine concentration, or motion of the patient. In order to receive these sensed parameters, control unit 520 may comprise, for example, an ECG monitor 524, connected to a site on the patient's body such as heart 530, for example using one or more subcutaneous sensors or ventricular and/or atrial intracardiac sensors. The control unit may also comprise an accelerometer 522 for detecting motion of the patient. Alternatively, ECG monitor 524 and/or accelerometer 522 comprise separate implanted devices placed external to control unit 520, and, optionally, external to the patient's body. Alternatively or additionally, control unit 520 receives signals from one or more physiological sensors 526, such as blood pressure sensors. Sensors 526 are typically implanted in the patient, for example in a left ventricle 532 of heart 530. In an embodiment, control unit 520 comprises or is coupled to an implanted device 525 for monitoring and correcting the heart rate, such as an implantable cardioverter defibrillator (ICD) or a pacemaker (e.g., a bi-ventricular or standard pacemaker). For example, implanted device 525 may be incorporated into a control loop executed by control unit 520, in order to increase the heart rate when the heart rate for any reason is too low.

FIG. 8A is a simplified cross-sectional illustration of a generally-cylindrical electrode device 540 applied to vagus nerve 536, in accordance with an embodiment of the present invention. Electrode device 540 comprises a central cathode 546 for applying a negative current ("cathodic current") in order to stimulate vagus nerve 536, as described below. Electrode device 540 additionally comprises a set of one or more anodes 544 (544a, 544b, herein: "efferent anode set 544"), placed between cathode 546 and the edge of electrode device 540 closer to heart 530 (the "efferent edge"). Efferent anode set 544 applies a positive current ("efferent anodal current") to vagus nerve 536, for blocking action potential conduction in vagus nerve 536 induced by the cathodic current, as described below. Typically, electrode device 540 comprises an additional set of one or more anodes 545 (545a, 545b, herein: "afferent anode set 545"), placed between cathode 546 and the edge of electrode device 540 closer to brain 534. Afferent anode set 545 applies a positive current ("afferent anodal current") to vagus nerve 536, in order to block propagation of action potentials in the direction of the brain during application of the cathodic current.

For some applications, the one or more anodes of efferent anode set 544 are directly electrically coupled to the one or more anodes of afferent anode set 545, such as by a common wire or shorted wires providing current to both anode sets substantially without any intermediary elements. Typically, coatings on the anodes, shapes of the anodes, positions of the anodes, sizes of the anodes and/or distances of the various anodes from the nerve are regulated so as to produce desired ratios of currents and/or desired activation functions delivered through or caused by the various anodes. For example, by varying one or more of these characteristics, the relative impedance between the respective anodes and central cathode 546 is regulated, whereupon more anodal current is driven through the one or more anodes having lower relative impedance. In these applications, central cathode 546 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Reference is now made to FIG. 8B, which is a simplified cross-sectional illustration of a generally-cylindrical electrode device 640 applied to vagus nerve 536, in accordance with an embodiment of the present invention. Electrode device 640 comprises exactly one efferent anode 644 and exactly one afferent anode 645, which are electrically coupled to each other, such as by a common wire 650 or shorted wires providing current to both anodes 644 and 645, substantially without any intermediary elements. The cathodic current is applied by a cathode 646 with an amplitude sufficient to induce action potentials in large- and medium-diameter fibers (e.g., A- and B-fibers), but insufficient to induce action potentials in small-diameter fibers (e.g., C-fibers).

Reference is again made to FIG. 8A. Cathodes 546 and anode sets 544 and 545 (collectively, "electrodes") are typically mounted in an electrically-insulating cuff 548 and separated from one another by insulating elements such as protrusions 549 of the cuff. Typically, the width of the electrodes is between about 0.5 and about 2 millimeters, or is equal to approximately one-half the radius of the vagus nerve. The electrodes are typically recessed so as not to come in direct contact with vagus nerve 536. For some applications, such recessing enables the electrodes to achieve generally uniform field distributions of the generated currents and/or generally uniform values of the activation function defined by the electric potential field in the vicinity of vagus nerve 524. Alternatively or additionally, protrusions 549 allow vagus nerve 524 to swell into the canals defined by the protrusions, while still holding the vagus nerve centered within cuff 548 and maintaining a rigid electrode geometry. For some applications, cuff 548 comprises additional recesses separated by protrusions, which recesses do not contain active electrodes. Such additional recesses accommodate swelling of vagus nerve 524 without increasing the contact area between the vagus nerve and the electrodes. For some applications, the distance between the electrodes and the axis of the vagus nerve is between about 1 and about 4 millimeters, and is greater than the closest distance from the ends of the protrusions to the axis of the vagus nerve. Typically, protrusions 549 are relatively short (as shown). For some applications, the distance between the ends of protrusions 549 and the center of the vagus nerve is between about 1 and 3 millimeters. (Generally, the diameter of the vagus nerve is between about 2 and 3 millimeters.) Alternatively, for some applications, protrusions 549 are longer and/or the electrodes are placed closer to the vagus nerve in order to reduce the energy consumption of electrode device 540.

In an embodiment of the present invention, efferent anode set 544 comprises a plurality of anodes 544, typically two anodes 544a and 544b, spaced approximately 0.5 to 2.0 millimeters apart. Application of the efferent anodal current in appropriate ratios from a plurality of anodes generally minimizes the "virtual cathode effect," whereby application of too large an anodal current stimulates rather than blocks fibers. In an embodiment, anode 544a applies a current with an amplitude equal to about 0.5 to about 5 milliamps (typically one-third of the amplitude of the current applied by anode 544b). When such techniques are not used, the virtual cathode effect generally hinders blocking of smaller-diameter fibers, as described below, because a relatively large anodal current is generally necessary to block such fibers.

Anode 544a is typically positioned in cuff 548 to apply current at the location on vagus nerve 536 where the virtual cathode effect is maximally generated by anode 544b. For applications in which the blocking current through anode 544b is expected to vary substantially, efferent anode set 544 typically comprises a plurality of virtual-cathode-inhibiting anodes 544a, one or more of which is activated at any time based on the expected magnitude and location of the virtual cathode effect.

Likewise, afferent anode set 545 typically comprises a plurality of anodes 545, typically two anodes 545a and 545b, in order to minimize the virtual cathode effect in the direction of the brain. In certain electrode configurations, cathode 546 comprises a plurality of cathodes in order to minimize the "virtual anode effect," which is analogous to the virtual cathode effect.

As appropriate, techniques described herein are practiced in conjunction with methods and apparatus described in U.S. patent application Ser. No. 10/205,474 to Gross et al., filed Jul. 24, 2002, entitled, "Electrode assembly for nerve control," which published as US Patent Publication 2003/0050677 and issued as U.S. Pat. No. 6,907,295, is assigned to the assignee of the present patent application, and is incorporated herein by reference. Alternatively or additionally, techniques described herein are practiced in conjunction with methods and apparatus described in U.S. patent application Ser. No. 10/205,475 to Gross at al., filed Jul. 24, 2002, entitled, "Selective nerve fiber stimulation for treating heart conditions," which published as US Patent Publication 2003/0045909, is assigned to the assignee of the present patent application, and is incorporated herein by reference. Further alternatively or additionally, techniques described herein are practiced in conjunction with methods and apparatus described in U.S. Provisional Patent Application 60/383,157 to Ayal et al., filed May 23, 2002, entitled, "Inverse recruitment for autonomic nerve systems," which is assigned to the assignee of the present patent application and is incorporated herein by reference.

FIG. 8C is a simplified perspective illustration of electrode device 540 (FIG. 8A), in accordance with an embodiment of the present invention. When applied to vagus nerve 536, electrode device 540 typically encompasses the nerve. As described, control unit 520 typically drives electrode device 540 to (i) apply signals to vagus nerve 536 in order to induce the propagation of efferent action potentials towards heart 530, and (ii) suppress artificially-induced afferent action potentials towards brain 534. The electrodes typically comprise ring electrodes adapted to apply a generally uniform current around the circumference of the nerve, as best shown in FIG. 8C.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Provisional Patent Application 60/383,157 to Ayal et al., filed May 23, 2002, entitled, "Inverse recruitment for autonomic nerve systems,"

International Patent Application PCT/IL02/00068 to Cohen et al., filed Jan. 23, 2002, entitled, "Treatment of disorders by unidirectional nerve stimulation," and U.S. patent application Ser. No. 10/488,334, in the national stage thereof, now U.S. Pat. No. 7,734,355, U.S. patent application Ser. No. 09/944,913 to Cohen and Gross, filed Aug. 31, 2001, entitled, "Treatment of disorders by unidirectional nerve stimulation," which issued as U.S. Pat. No. 6,684,105, U.S. patent application Ser. No. 09/824,682 to Cohen and Ayal, filed Apr. 4, 2001, entitled "Method and apparatus for selective control of nerve fibers," now U.S. Pat. No. 6,600,954, U.S. patent application Ser. No. 10/205,475 to Gross et al., filed Jul. 24, 2002, entitled, "Selective nerve fiber stimulation for treating heart conditions," now U.S. Pat. No. 7,778,703, U.S. patent application Ser. No. 10/205,474 to Gross et al., filed Jul. 24, 2002, entitled, "Electrode assembly for nerve control," which issued as U.S. Pat. No. 6,907,295, International Patent Application PCT/IL03/00431 to Ayal at al., filed May 23, 2003, entitled, "Selective nerve fiber stimulation for treating heart conditions,"

International Patent Application PCT/IL03/00430 to Ayal et al., filed May 23, 2003, entitled, "Electrode assembly for nerve control," and U.S. patent application Ser. No. 10/529,149, in the national stage thereof, now abandoned, U.S. patent application Ser. No. 10/719,659 to Ben David et al., filed Nov. 20, 2003, entitled, "Selective nerve fiber stimulation for treating heart conditions," now U.S. Pat. No. 7,778,711, U.S. patent application Ser. No. 11/022,011 to Cohen et al., filed Dec. 22, 2004, entitled, "Construction of electrode assembly for nerve control," now U.S. Pat. No. 7,561,922, U.S. patent application Ser. No. 11/234,877 to Ben-David et al., filed Sep. 22, 2005, entitled, "Selective nerve fiber stimulation," now U.S. Pat. No. 7,885,709, and U.S. patent application Ser. No. 11/280,884 to Ayal et al., filed Nov. 15, 2005, entitled, "Techniques for nerve stimulation," which published as US Patent Application Publication 2006/0106441.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for application to a nerve of a subject, comprising an electrode cuff, which comprises:
   a housing, configured to be placed at least partially around the nerve so as to define an inner surface of the housing that faces the nerve;
   a plurality of insulating elements coupled to the inner surface of the housing at respective insulating element longitudinal positions along the housing, such that the inner surface of the housing and pairs of the insulating elements define one or more respective cavities at respective cavity longitudinal positions along the housing; and
   one or more electrodes, fixed to the housing in fewer than all of the cavities, such that at least one of the cavities is an empty cavity that does not have an electrode positioned therein,
   wherein the housing has a length of between 10 mm and 14 mm, an outer radius of between 4 mm and 8 mm, an inner radius of between 3 mm and 6 mm,
   wherein the insulating elements have an outer radius of between 3 mm and 6 mm, and an inner radius of between 2 mm and 3.5 mm, and
   wherein the plurality of insulating elements comprises exactly seven insulating elements, respective edges of which are positioned within the housing at the following respective distances from one end of the housing: 0.0 mm, between 1.3 and 1.7 mm, between 2.7 and 3.3 mm, between 5.1 and 6.3 mm, between 7.1 and 8.7 mm, between 8.5 and 10.3 mm, and between 10.2 and 12.4 mm, and the insulating elements having the following respective widths: between 0.7 and 0.9 mm, between 0.7 and 0.9 mm, between 1.4 and 1.8 mm, between 0.7 and 0.9 mm, between 0.7 and 0.9 mm, between 1.1 and 1.3 mm, and between 0.7 and 0.9 mm.

2. The apparatus according to claim 1, further comprising a control unit, coupled to the electrodes, and configured to drive at least a portion of the electrodes to apply a current to the nerve.

3. The apparatus according to claim 2, wherein the electrodes comprise two or more cathode electrodes, and wherein the empty cavity is between and directly adjacent along the cuff to two cavities containing two respective ones of the cathode electrodes.

4. The apparatus according to claim 2, wherein the electrodes comprise two or more anode electrodes, and wherein the empty cavity is between and directly adjacent along the cuff to two cavities containing two respective ones of the anode electrodes.

5. The apparatus according to claim 2, wherein the electrodes comprise two or more cathode electrodes and one or more anode electrodes, and wherein the empty cavity is between and directly adjacent along the cuff to two cavities containing two respective ones of the cathode electrodes.

6. The apparatus according to claim 2, wherein the electrodes comprise two or more anode electrodes and one or more cathode electrodes, and wherein the empty cavity is between and directly adjacent along the cuff to two cavities containing two respective ones of the anode electrodes.

7. The apparatus according to claim 2, wherein the plurality of electrodes comprises at least one cathode electrode, at least one anode electrode, and two or more passive electrodes, and wherein the apparatus further comprises a conducting element, which electrically couples the passive electrodes to one another.

8. The apparatus according to claim 7,
   wherein the exactly seven insulating elements are arranged along the housing such that the inner surface of the housing and the pairs of insulating elements define first, second, third, fourth, fifth, and sixth cavities, the first cavity closest to the one end of the housing, the second adjacent to the first, the third adjacent to the second, the fourth adjacent to the third, the fifth adjacent to the fourth, and the sixth adjacent to the fifth,
   wherein the at least one cathode electrode comprises at least one first cathode electrode and at least one second cathode electrode,
   wherein at least a first one of the passive electrodes is fixed to the housing in the first cavity,
   wherein the at least one anode electrode is fixed to the housing in the second cavity,
   wherein the at least one first cathode electrode is fixed to the housing in the third cavity, wherein no electrodes are fixed to the housing in the fourth cavity, wherein the at least one second cathode electrode is fixed to the housing in the fifth cavity, and wherein at least a second one of the passive electrodes is fixed to the housing in the sixth cavity.

9. The apparatus according to claim 1, wherein the insulating elements are shaped so as to define respective contact surfaces, and wherein the housing and the insulating elements are configured such that the contact surfaces are suitable for being positioned less than 0.5 mm from a surface of the nerve when the housing is placed at least partially around the nerve.

10. The apparatus according to claim 1, wherein the insulating elements are shaped so as to define respective contact surfaces, and wherein the housing and the insulating elements are configured such that the contact surfaces are suitable for at least partially coming in physical contact with the nerve when the housing is placed at least partially around the nerve.

11. The apparatus according to claim 1, wherein a length that at least one of the insulating elements protrudes from the housing toward a central axis of the cuff is at least 0.5 mm.

12. The apparatus according to claim 1, wherein the electrodes are fixed to the housing in a number of the cavities, wherein a difference between the number of the cavities and a total number of the cavities is an integer between 1 and 3, inclusive, such that between 1 and 3 of the cavities do not have any of the electrodes fixed therein.

13. The apparatus according to claim 1, wherein at least two of the electrodes are fixed to the housing in one of the cavities.

14. The apparatus according to claim 1, wherein the electrodes comprise ring electrodes.

15. The apparatus according to claim 1, wherein the electrodes are fixed to the housing in at least two of the cavities.

16. The apparatus according to claim 15, wherein the electrodes are fixed to the housing in at least three of the cavities.

17. A method comprising:

placing, at least partially around a nerve, an electrode cuff, which includes (a) a housing, configured to be placed at least partially around the nerve so as to define an inner surface of the housing that faces the nerve, (b) a plurality of insulating elements coupled to the inner surface of the housing at respective insulating element longitudinal positions along the housing, such that the inner surface of the housing and pairs of the insulating elements define one or more respective cavities at respective cavity longitudinal positions along the housing, and (c) one or more electrodes, fixed to the housing in fewer than all of the cavities, such that at least one of the cavities is an empty cavity that does not have an electrode positioned therein, wherein the housing has a length of between 10 mm and 14 mm, an outer radius of between 4 mm and 8 mm, an inner radius of between 3 mm and 6 mm, wherein the insulating elements have an outer radius of between 3 mm and 6 mm, and an inner radius of between 2 mm and 3.5 mm, and wherein the plurality of insulating elements comprises exactly seven insulating elements, respective edges of which are positioned within the housing at the following respective distances from one end of the housing: 0.0 mm, between 1.3 and 1.7 mm, between 2.7 and 3.3 mm, between 5.1 and 6.3 mm, between 7.1 and 8.7 mm, between 8.5 and 10.3 mm, and between 10.2 and 12.4 mm, and the insulating elements having the following respective widths: between 0.7 and 0.9 mm, between 0.7 and 0.9 mm, between 1.4 and 1.8 mm, between 0.7 and 0.9 mm, between 0.7 and 0.9 mm, between 1.1 and 1.3 mm, and between 0.7 and 0.9 mm; and applying a current to the nerve using at least a portion of the electrodes.

* * * * *